US007544312B2

(12) United States Patent
Herron et al.

(10) Patent No.: US 7,544,312 B2
(45) Date of Patent: Jun. 9, 2009

(54) CHARGE TRANSPORT COMPOSITIONS AND ELECTRONIC DEVICES MADE WITH SUCH COMPOSITIONS

(76) Inventors: Norman Herron, 408 Apple Rd., Newark, DE (US) 19711; Nora Sabina Radu, 109 Stoney Ridge Rd., Landenberg, PA (US) 19350; Eric M. Smith, 103 W. Sutton Pl., Wilmington, DE (US) 19810; Ying Wang, 4010 Greenmount Rd., Wilmington, DE (US) 19810

( * ) Notice: Subject to any disclaimer, the term of this patent is extended or adjusted under 35 U.S.C. 154(b) by 0 days.

(21) Appl. No.: 11/676,401

(22) Filed: Feb. 19, 2007

(65) Prior Publication Data

US 2007/0194698 A1 Aug. 23, 2007

Related U.S. Application Data

(62) Division of application No. 10/612,244, filed on Jul. 2, 2003, now abandoned.

(60) Provisional application No. 60/394,767, filed on Jul. 10, 2002, provisional application No. 60/458,277, filed on Mar. 28, 2003, now abandoned.

(51) Int. Cl.
*H01B 1/12* (2006.01)

(52) U.S. Cl. ...................................... 252/500; 564/336

(58) Field of Classification Search ................. 252/500, 252/301.16; 564/336
See application file for complete search history.

(56) References Cited

U.S. PATENT DOCUMENTS

| | | | |
|---|---|---|---|
| 3,423,427 | A | 1/1969 | Cescon et al. |
| 3,449,379 | A | 6/1969 | Cescon et al. |
| 3,666,466 | A | 5/1972 | Striko |
| 3,739,000 | A | 6/1973 | Lodolini et al. |
| 4,140,529 | A | 2/1979 | Pai et al. |
| 4,304,829 | A | 12/1981 | Limburg et al. |
| 6,004,709 | A | 12/1999 | Renfer et al. |

FOREIGN PATENT DOCUMENTS

| | | |
|---|---|---|
| FR | 2 099 783 | 3/1972 |
| GB | 1047796 | 11/1966 |

OTHER PUBLICATIONS

Malpert. John H. et al., Color intensity control in polymers using triarylmethane leuconitriles as color formers, Tetrahedron, 2001, 967-974, 57, Elsevier Science Ltd.

Kuder, James E. et al., Anodic and Photochemical Oxidation of Triphenylmethanes, J. Org. Chem., 1979, 761-766, 44(5), American Chemical Society.

Gruenbaum, W. T. et al., Hole Transport in Triphenylmethans Dopad Polymers, Jpn. J. Appl. Phys., May 1996, 2704-2708, vol. 35, Pt. 1, No. 5A.

(Continued)

*Primary Examiner*—Mark Kopec
(74) *Attorney, Agent, or Firm*—John H. Lamming

(57) ABSTRACT

The present invention relates to charge transport compositions. The invention further relates to electronic devices in which there is at least one active layer comprising such charge transport compositions.

13 Claims, 14 Drawing Sheets

$$X_5Ar^1—C(—Ar^1—NR^1_2)(—Ar^1—NR^1_2)—H \quad (I)$$

OTHER PUBLICATIONS

Borsenberger, P.M. et al., Hole Transport in Vapor-Deposited Triphenylmethane Glasses, Jpn. J. Appl. Phys., May 1996, 2698-2703, vol. 35, Pt. 1, No. 5A.

Borsenberger, Paul M. et al., Effects of the Dipole Moment on Charge Transport in Disordered Molecular Solids, The Journal of Physical Chemistry, 1993. 4816-4819, 97(18), American Chemical Society.

Gibson, Harry W. et al.. Surface Analyses by a Triboelectric Charging Techniques, Analytical Chemistry, Apr. 1979. 483-487, 51(4), American Chemical Society.

Young, Ralph H. et al., Dipole Moments of Hole-Transporting Materials and Their Influence on Hole Mobility in Molecularly Doped Polymers, J. Phys. Chem., 1995, 4230-4240, 99(12), American Chemical Society.

I(a)

I(b)

I(c)

I(d)

I(e)

I(f)

I(g)

I(h)

I(i)

I(j)

I(k)

I(l)

I(m)

I(n)

I(o)

I(p)

I(q)

I(r)

I(s)

III(a)

III(b)

III(c)

III(d)

III(e)

III(f)

III(g)

III(h)

FIG. 5A
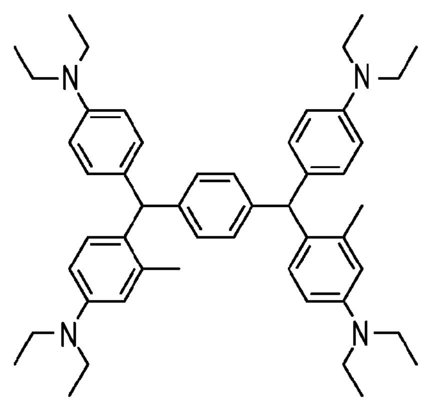
II(a)
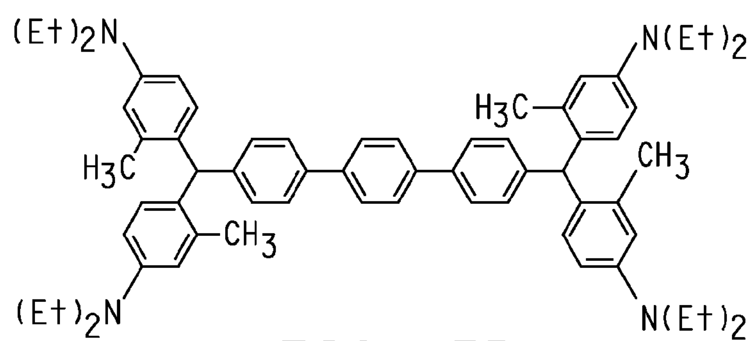
II(b)
FIG. 5B
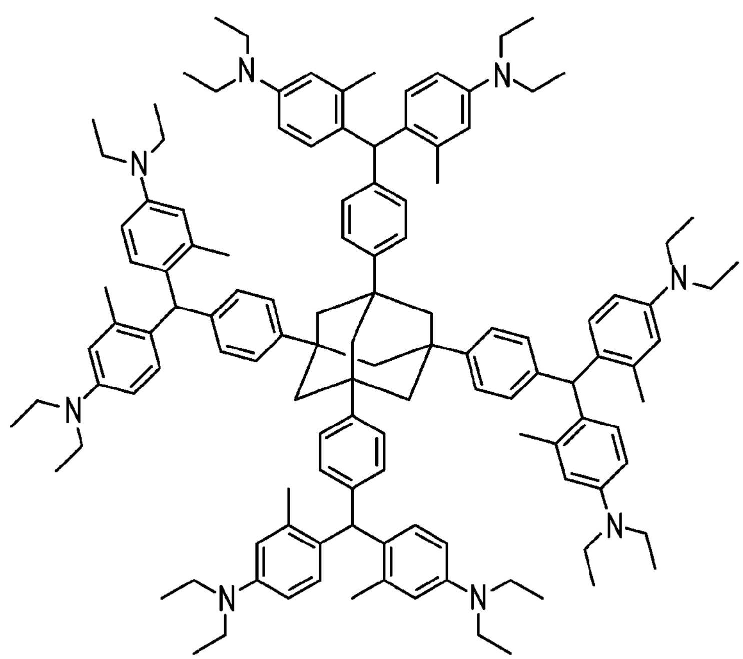
II(c)
FIG. 5C

II(d)

II(e)

II(f)

IV(a)

IV(b)

IV(c)

IV(d)

IV(e)

MPMP
(Compound A)

TPD
(Compound B)

MTDATA
(Compound C)

NPB
(Compound D)

CBP
(Compound E)

CHARGE TRANSPORT COMPOSITIONS AND ELECTRONIC DEVICES MADE WITH SUCH COMPOSITIONS

CROSS REFERENCE TO RELATED APPLICATIONS

This application is a division of U.S. application Ser. No. 10/612,244 filed Jul. 2, 2003, now abandoned, and claims priority from U.S. Provisional Application Ser. No. 60/394,767, filed Jul. 10, 2002, and U.S. Provisional Application Ser. No. 60/458,277, filed Mar. 28, 2003, now abandoned both of which are incorporated by reference herein in their entirety.

BACKGROUND OF THE INVENTION

1. Field of the Invention

The present invention relates to charge transport compositions. The invention further relates to photoactive electronic devices in which there is at least one active layer comprising such charge transport compositions.

2. Background

In organic photoactive electronic devices, such as light-emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices which use photoactive materials, frequently include one or more charge transport layers, which are positioned between the photoactive (e.g., light-emitting) layer and one of the contact layers. A hole transport layer may be positioned between the photoactive layer and the hole-injecting contact layer, also called the anode. An electron transport layer may be positioned between the photoactive layer and the electron-injecting contact layer, also called the cathode.

There is a continuing need for charge transport materials.

SUMMARY OF THE INVENTION

The present invention is directed to a charge transport composition comprising a triarylmethane having Formula I, shown in FIG. 1, wherein:

$Ar^1$ can be the same or different at each occurrence and is selected from aryl and heteroaryl;

$R^1$ can be the same or different at each occurrence and is selected from H, alkyl, heteroalkyl, aryl, heteroaryl, arylalkylene, heteroarylalkylene, $C_nH_aF_b$, and $C_6H_cF_d$, or adjacent $R^1$ groups can be joined to form 5- or 6-membered rings;

X can be the same or different at each occurrence and is selected from $R^1$, alkenyl, alkynyl, $N(R^1)_2$, $OR^1$, $OC_nH_aF_b$, $OC_6H_cF_d$, halide, $NO_2$, OH, CN, and $COOR^1$;

n is an integer, and a, b, c, and d are 0 or an integer such that a+b=2n+1, and c+d=5.

In another embodiment, the present invention is directed to a charge transport composition comprising the above triarylmethane, with the proviso that there is at least one substitutent on an aromatic group selected from F, $C_nH_aF_b$, $OC_nH_aF_b$, $C_6H_cF_d$, and $OC_6H_cF_d$.

In another embodiment, the present invention is directed to a charge transport composition with at least one triarylmethane carbon, having Formula II shown in FIG. 2, wherein:

$R^2$ is the same or different at each occurrence and is selected from arylene, heteroarylene, arylenealkylene, and heteroarylenealkylene, with the proviso that when $R^2$ is arylenealkylene or heteroarylenealkylene, an arylene end is attached to the triarylmethane carbon;

Q is selected from a single bond and a multivalent group;

m is an integer equal to at least 2;

p is 0 or 1, with the proviso that when p is 0, Q is a multivalent group that is arylene or heteroarylene; and $Ar^1$, $R^1$, a through d, and n are as defined above.

In another embodiment, the present invention is directed to an electronic device having at least one layer comprising a material selected from Formulae I and II, shown in FIGS. 1 and 2, wherein $Ar^1$, $R^1$, $R^2$, Q, X, a through d, m, n, and p are as defined above, with the proviso that in Formula I when $X_5Ar^1$ is p-methylphenylene, $R^1$ is not ethyl.

As used herein, the term "charge transport composition" is intended to mean material that can receive a charge from an electrode and facilitate its movement through the thickness of the material with relatively high efficiency and small loss of charge. Hole transport compositions are capable of receiving a positive charge from an anode and transporting it. Electron transport compositions are capable of receiving a negative charge from a cathode and transporting it. The term "anti-quenching composition" is intended to mean a material which prevents, retards, or diminishes both the transfer of energy and the transfer of an electron to or from the excited state of the photoactive layer to an adjacent layer. The term "photoactive" refers to any material that exhibits electroluminescence, photoluminescence, and/or photosensitivity. The term "HOMO" refers to the highest occupied molecular orbital of a compound. The term "LUMO" refers to the lowest unoccupied molecular orbital of a compound. The term "group" is intended to mean a part of a compound, such as a substitutent in an organic compound. The prefix "hetero" indicates that one or more carbon atoms has been replaced with a different atom. The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted. The terms "heteroalkenyl", "heteroalkenylene", "heteroalkynyl" and "heteroalkynlene" are intended to mean analogous groups having one or more heteroatoms. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted. The terms "heteroalkenyl", "heteroalkenylene", "heteroalkynyl" and "heteroalkynlene" are intended to mean analoguse groups having one or more heteroatoms. The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted. The term "arylalkylene" is intended to mean a group derived from an alkyl group having an aryl substitutent, which group may be further unsubstituted or substituted. The term "heteroarylalkylene" is intended to mean a group derived from an alkyl group having a heteroaryl substitutent, which group may be further unsubstituted or substituted. The term "arylene" is intended to mean a group derived from an aromatic hydrocarbon having two points of attachment, which group may be unsubstituted or substituted. The term "heteroarylene" is intended to mean a group derived from an aromatic group having at least one heteroatom and having two points of attachment, which group may be unsubstituted or substituted. The term "arylenealkylene" is intended to mean a group having both aryl and alkyl groups and having one point of attachment on an aryl group and one point of attachment on an alkyl group. The term "heteroarylenealkylene" is intended to mean a group having both aryl and alkyl groups and having one point of attachment on an aryl group and one point of attachment on an alkyl group, and in which there is at least one heteroatom. Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "polymeric" is intended to encompass oligomeric species and include materials having 2 or more monomeric units. In addition, the IUPAC numbering system is used throughout, where the groups from the Periodic Table are numbered from left to right as 1 through 18 (CRC Handbook of Chemistry and Physics, $81^{st}$ Edition, 2000).

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE PREFERRED EMBODIMENTS

Figure 1:
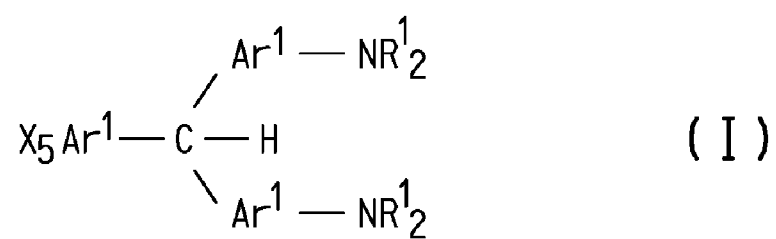
FIG. 1 shows Formula I for a charge transport composition of the invention.

The triarylmethane compounds represented by Formula I, shown in FIG. 1, have particular utility as hole transport compositions. The compound bis(4-N,N-diethylamino-2-methylphenyl)-4-methylphenylmethane (MPMP) has been disclosed to be a suitable hole transport composition in Petrov et al., Published PCT application WO 02/02714. Other triarylmethane derivatives have not been used in OLED devices.

In general, n is an integer. In one embodiment, n is an integer from 1 through 20. In one embodiment, n is an integer from 1 through 12.

In one embodiment, $Ar^1$ is selected from phenyl and biphenyl groups, which may have one or more carbon atoms replaced with a heteroatom. All of these groups may further be substituted. Examples of substitutents include, but are not limited to, alkyl, heteroalkyl, aryl, heteroaryl, arylalkylene, heteroarylalkylene, $C_nH_aF_b$, and $C_6H_cF_d$, where a through d and n are as defined above.

In one embodiment, the $Ar^1$ in the $X_5Ar^1$ group is selected from phenyl, biphenyl, pyridyl, and bipyridyl, which may further be substituted. Examples of substitutents include, but are not limited to, alkyl, heteroalkyl, aryl, heteroaryl, arylalkylene, heteroarylalkylene, $C_nH_aF_b$, and $C_6H_cF_d$, where a through d and n are as defined above.

In one embodiment, X is a fused heteroaromatic ring group. Examples of such groups include, but are not limited to, N-carbazoles, benzodiazoles, and benzotriazoles.

In one embodiment, $N(R^1)_2$ is a fused heteroaromatic ring group. Examples of such groups include, but are not limited to, carbazoles, benzodiazoles, and benzotriazoles.

In one embodiment $R^1$ is selected from alkyl groups having 1 through 12 carbon atoms, phenyl and benzyl.

In one embodiment, there is at least one substituent on an aryl ring selected from F, $C_nH_aF_b$, $OC_nH_aF_b$, $C_6H_cF_d$, and $OC_6H_cF_d$, where a through d and n are as defined above.

In one embodiment, there is at least one X group selected from F, $C_nH_aF_b$, $OC_nH_aF_b$, $C_6H_cF_d$, and $OC_6H_cF_d$, where a through d and n are as defined above.

Examples of suitable hole transport compounds of the invention include, but are not limited to, those given as Formulae I(a) through I(t), shown in FIG. 3.

The compositions represented by Formula I can be prepared using standard synthetic organic techniques, as illustrated in the examples. The compounds can be applied as thin films by evaporative techniques or conventional solution processing methods. As used herein, "solution processing" refers to the formation of films from a liquid medium. The liquid medium can be in the form of a solution, a dispersion, an emulsion, or other forms. Typical solution processing techniques include, for example, solution casting, drop casting, curtain casting, spin-coating, screen printing, inkjet printing, gravure printing, and the like.

Figure 2:
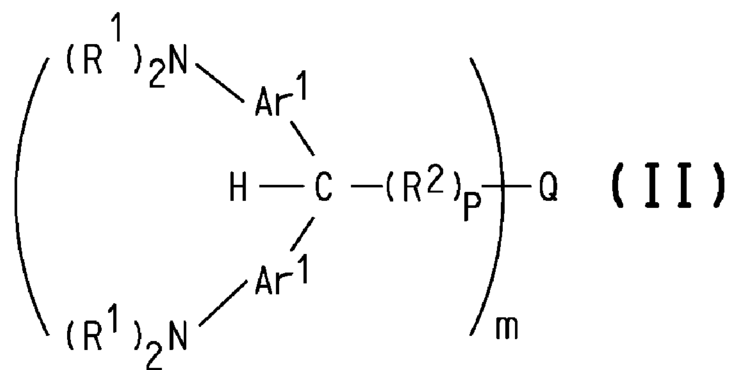
FIG. 2 shows Formula II for a charge transport composition of the invention.
Figure 3A:
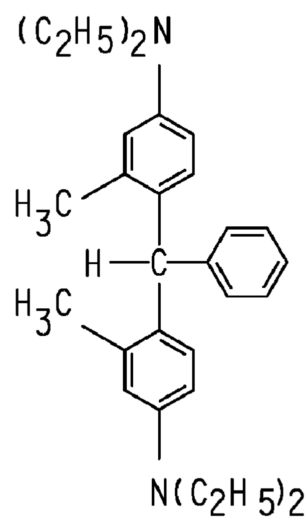
FIG. 3 shows Formulae I(a) through I(s) for a charge transport composition of the invention.
Figure 3B:
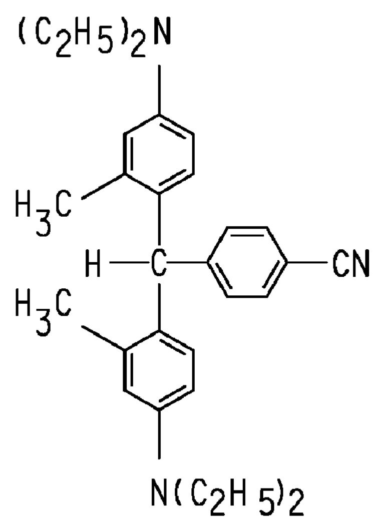
Figure 3C:
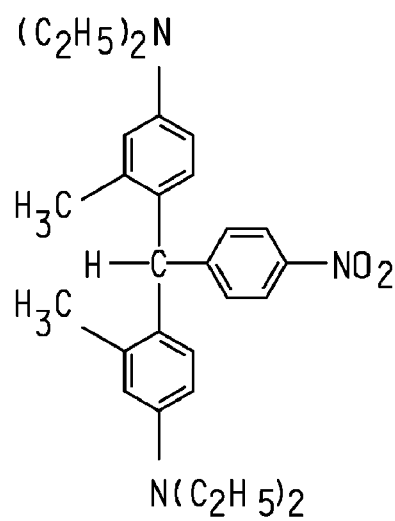
Figure 3D:
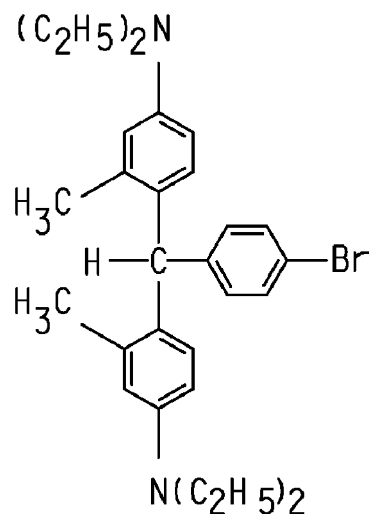
Figure 3E:
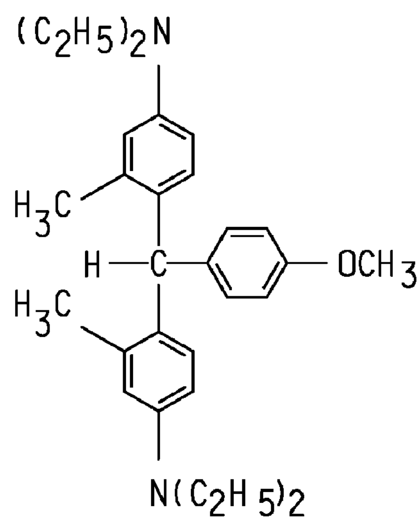
Figure 3F:
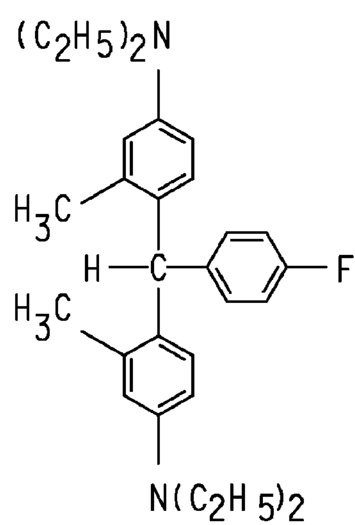
Figure 3G:
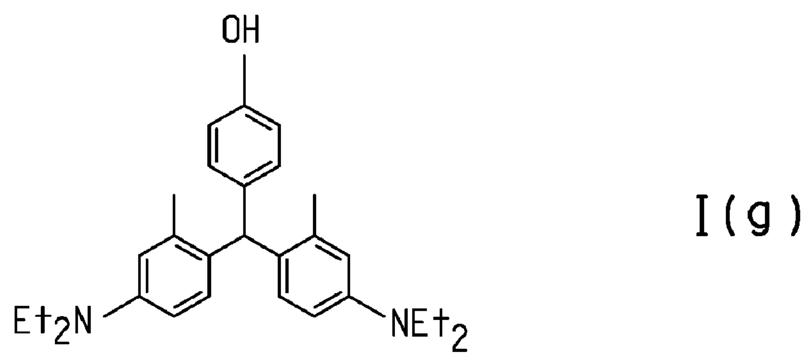
Figure 3H:
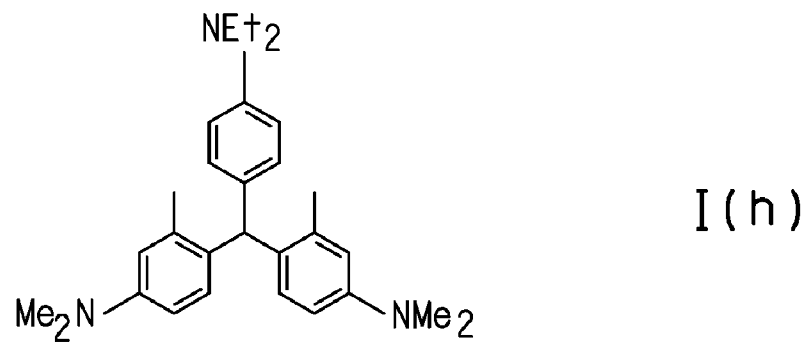
Figure 3I:
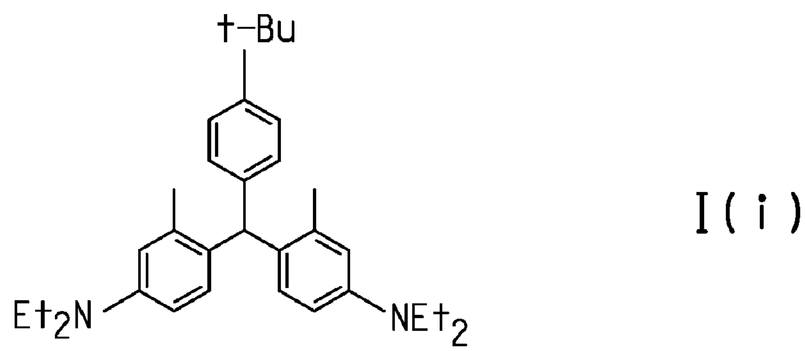
Figure 3J:
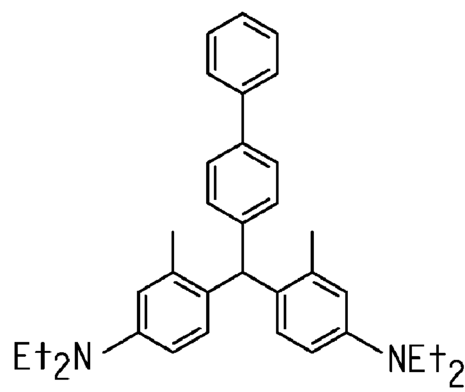
Figure 3K:
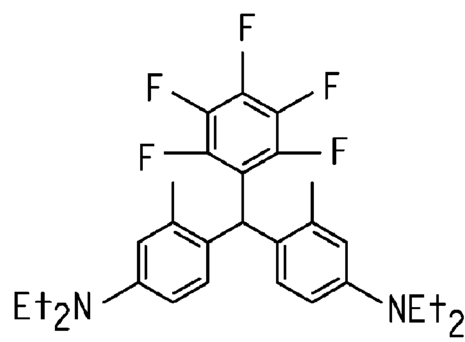
Figure 3L:
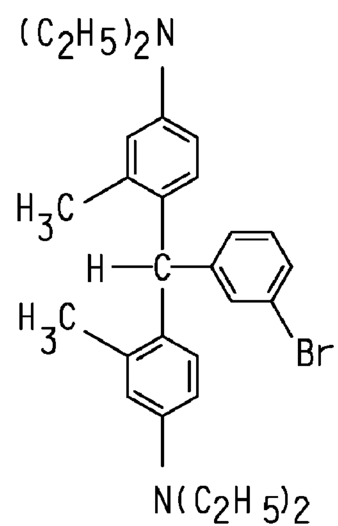
Figure 3M:
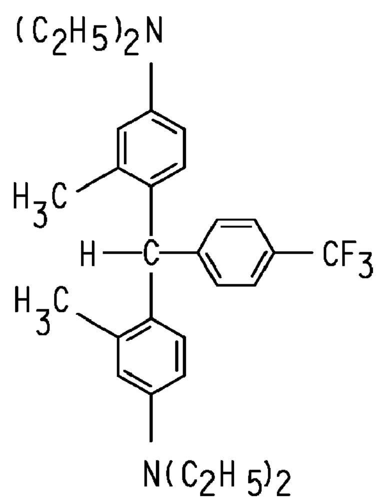
Figure 3N:
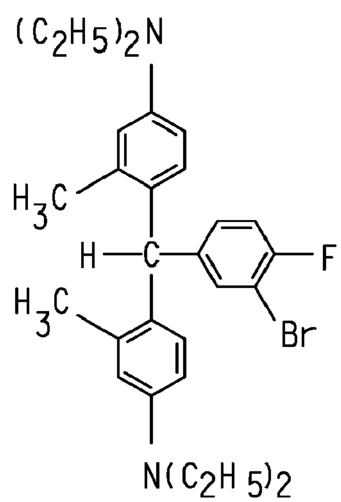
Figure 3O:
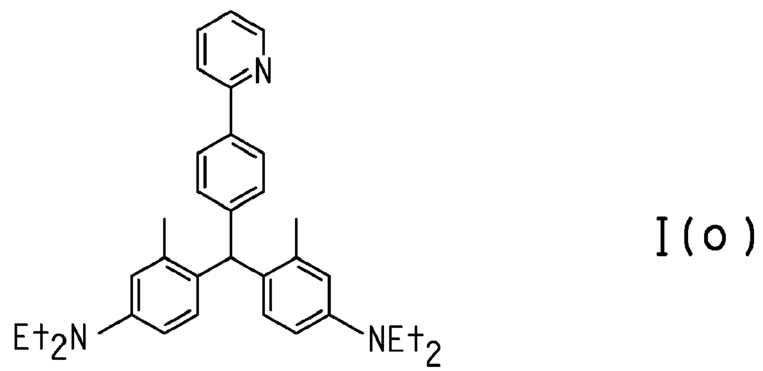
Figure 3P:
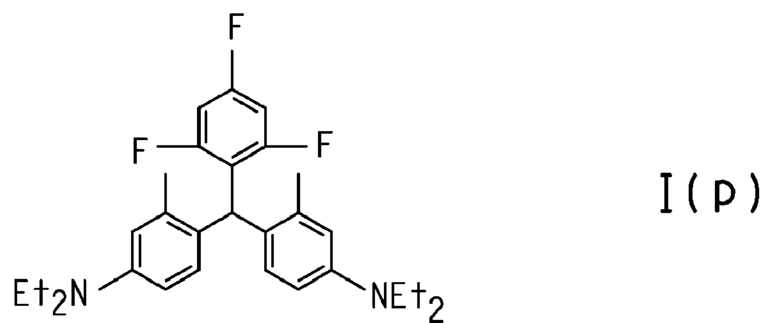
Figure 3Q:
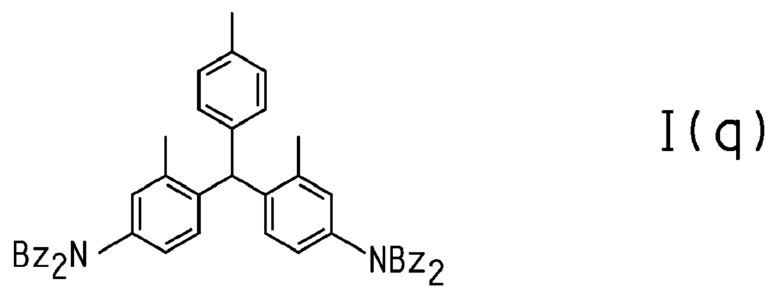
Figure 3R:
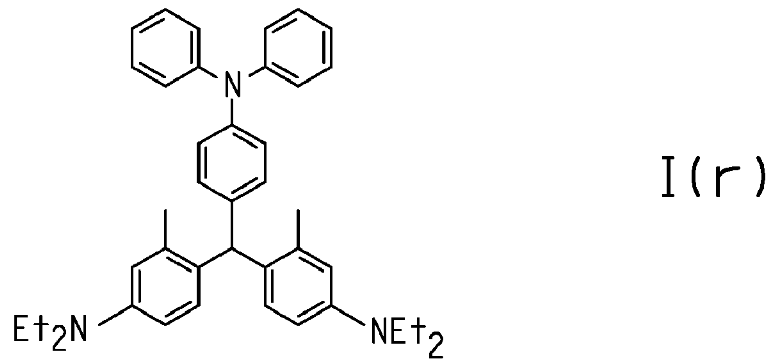
Figure 3S:
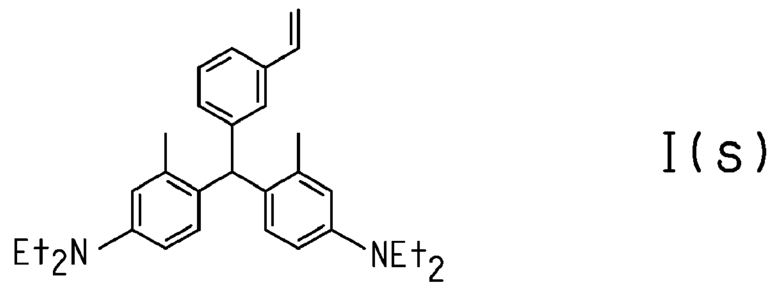
Figure 4A:
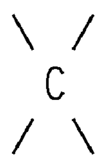
FIG. 4 shows Formulae III(a) through III(h) for a multidentate linking group.
Figure 4B:
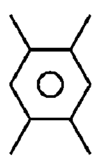
Figure 4C:
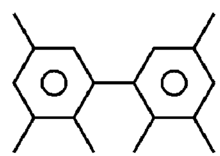
Figure 4D:
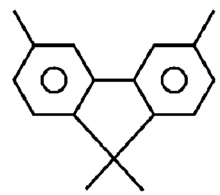
Figure 4E:
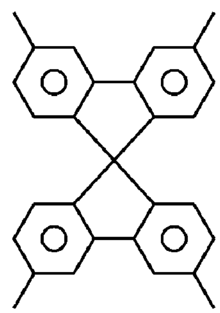
Figure 4F:
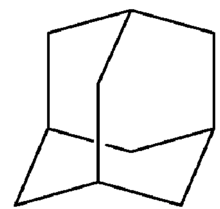
Figure 4G:
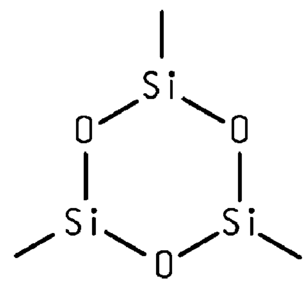
Figure 4H:
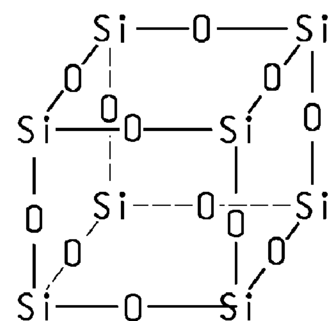

In some cases it is desirable to increase the Tg of the compounds to improve stability, coatability, and other properties. This can be accomplished by linking together two or more of the compounds with a linking group to form compounds having Formula II, shown in FIG. 2. In Formula II, the carbon atom shown as "C" is referred to as a "triarylmethane carbon". In this formula, Q can be a single bond or a multivalent linking group, having two or more points of attachment. The multivalent linking group can be a hydrocarbon group with two or more points of attachment, and can be aliphatic or aromatic. The multivalent linking group can be a heteroalkyl or heteroaromatic group, where the heteroatoms can be, for example, N, O, S, or Si. Examples of multivalent groups, Q, include, but are not limited to, alkylene, alkenylene, and alkynylene groups, and analogous compounds with heteroatoms; single, multiple-ring, and fused-ring aromatics and heteroaromatics; arylamines, such as triarylamines; silanes and siloxanes. Additional examples of multivalent Q groups are given in FIG. 4 as Formulae III(a) through III(h). In Formula III(f), any of the carbons may be linked to a charge transport moiety. In Formula III(h), any of the Si atoms can be linked to a charge transport moiety. Heteroatoms such as Ge and Sn can also be used. The linking group can also be $—[SiMeR^1—SiMeR^1]_n—$, where $R^1$ and n are as defined above.

In general, m is an integer equal to at least 2. The exact number depends on the number of available linking positions on Q and on the geometries of the triarylmethane moiety and Q. In one embodiment, m is an integer from 2 through 10.

In general, n is an integer. In one embodiment, n is an integer from 1 through 20. In one embodiment, n is an integer from 1 through 12.

In one embodiment, $Ar^1$ is selected from phenyl and biphenyl groups, which may have one or more carbon atoms replaced with a heteroatom. All of these groups may further be substituted. Examples of substitutents include, but are not limited to, alkyl, heteroalkyl, aryl, heteroaryl, arylalkylene, heteroarylalkylene, $C_nH_aF_b$, and $C_6H_cF_d$, where a through d and n are as defined above.

In one embodiment, $N(R^1)_2$ is a fused heteroaromatic ring group. Examples of such groups include, but are not limited to, carbazoles, benzodiazoles, and benzotriazoles.

In one embodiment $R^1$ is selected from alkyl groups having 1 through 12 carbon atoms, phenyl and benzyl.

In one embodiment, $R^2$ is selected from phenyl, biphenyl, pyridyl, and bipyridyl, which may further be substituted. Examples of substitutents include, but are not limited to, alkyl, heteroalkyl, aryl, heteroaryl, arylalkylene, heteroarylalkylene, $C_nH_aF_b$, and $C_6H_cF_d$, where a through d and n are as defined above.

In one embodiment, at least one $R^1$ is selected from F, $C_nH_aF_b$, $OC_nH_aF_b$, $C_6H_cF_d$, and $OC_6H_cF_d$, where a through d and n are as defined above.

The compositions represented by Formula II can be prepared using standard synthetic organic techniques, as illustrated in the examples. The compounds can be applied as thin films by evaporative techniques or conventional solution processing methods. As used herein, "solution processing" refers to the formation of films from a liquid medium. The liquid medium can be in the form of a solution, a dispersion, an emulsion, or other forms. Typical solution processing techniques include, for example, solution casting, drop casting, curtain casting, spin-coating, screen printing, inkjet printing, gravure printing, and the like.

Figure 5D:
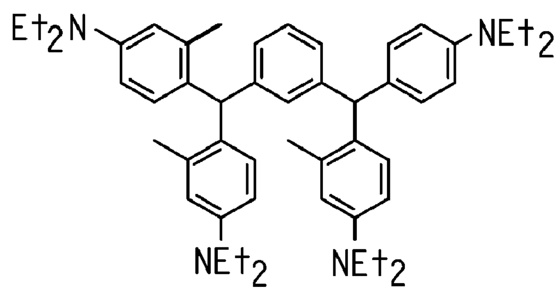
FIG. 5 shows Formulae II(a) through II(f) for a charge transport composition of the invention.
Figure 5E:
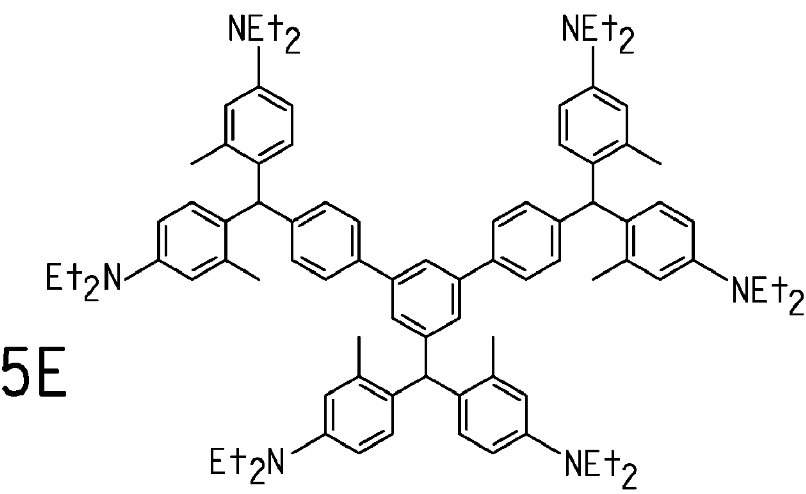
Figure 5F:
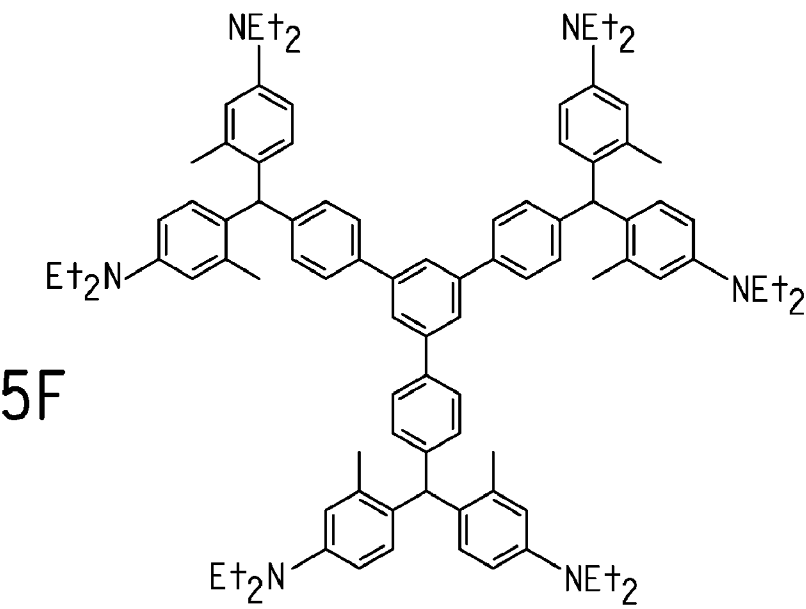
Figure 6A:
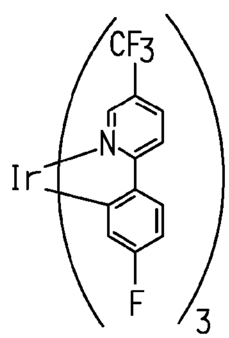
FIG. 6 shows Formulae IV(a) through IV(e) for electroluminescent iridium complexes.
Figure 6B:
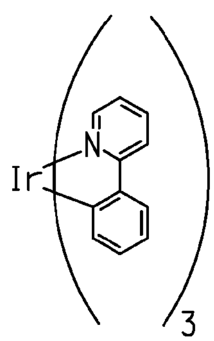
Figure 6C:
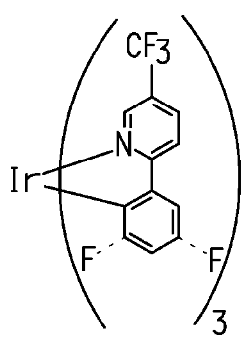
Figure 6D:
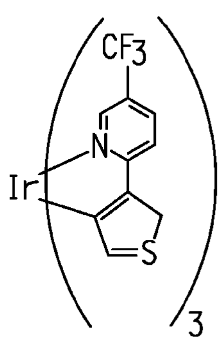
Figure 6E:
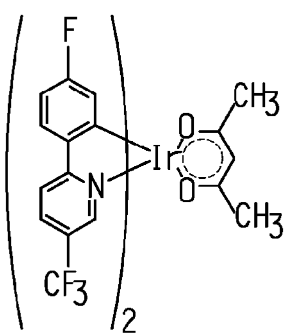
Figure 8A:
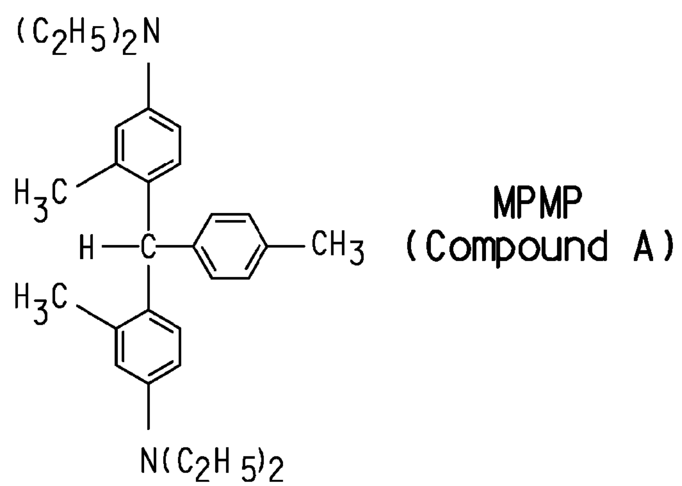
FIG. 8 is shows formulae for known hole transport materials.
Figure 8B:
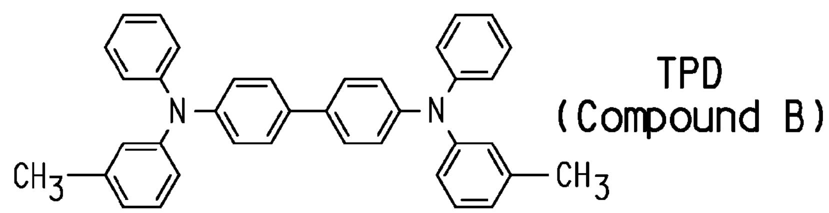
Figure 8C:
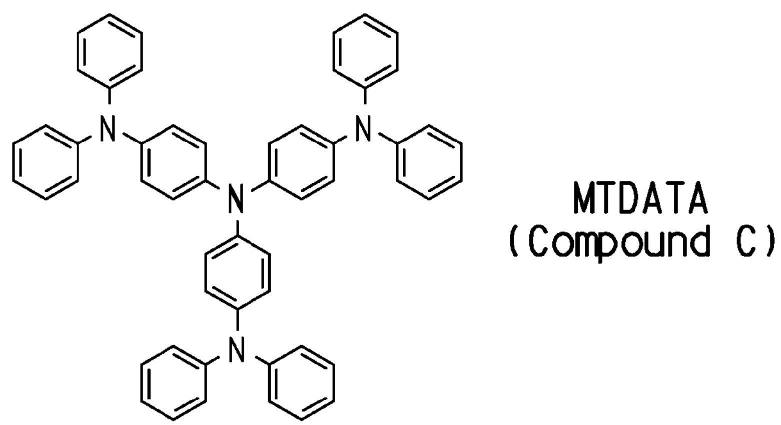
Figure 8D:
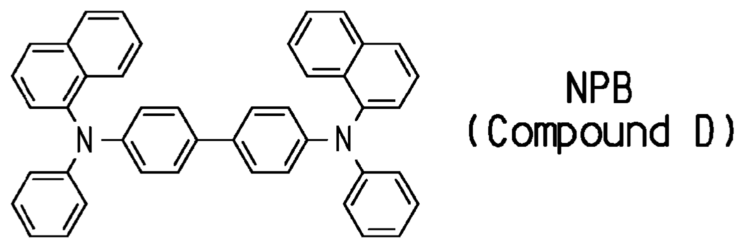
Figure 8E:
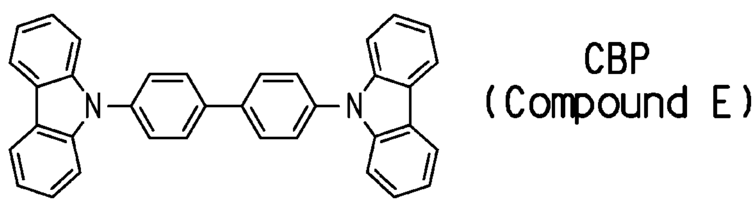

Examples of linked compounds having Formula II include, but are not limited to, those given in FIG. 5, Formulae II(a) through II(h).

Electronic Device

Figure 7:
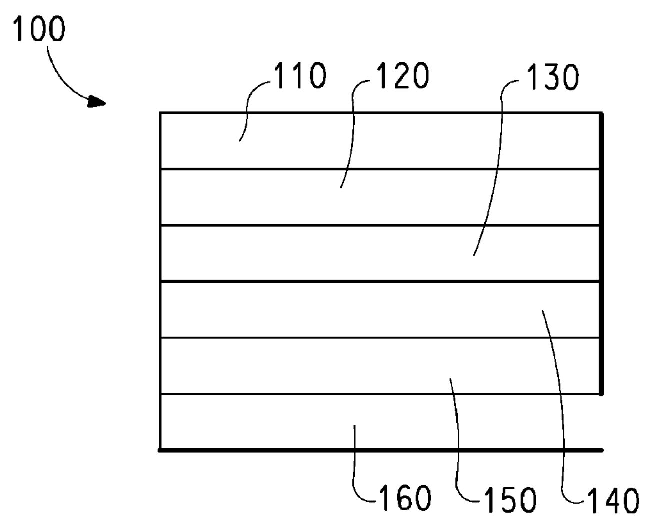
FIG. 7 is a schematic diagram of a light-emitting diode (LED).

The present invention also relates to an electronic device comprising at least one of the charge transport compositions of the invention. The charge transport compositions can be in a separate layer, positioned between a photoactive layer and one electrode. Alternatively, the charge transport compositions of the invention can be in the photoactive layer. A typical device structure is shown in FIG. 7. The device 100 has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. As an option, devices frequently use another electron transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary,* 470 and 476 (McGraw-Hill, Inc. 1966).

The triarylmethane derivative compounds of the invention are particularly useful as the hole transport layer 120, and as a charge conducting host in the photoactive layer, 130. The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature* vol. 357, pp 477-479 (11 Jun. 1992). At least one of the anode and cathode should be at least partially transparent to allow the generated light to be observed.

Examples of the photoactive layer 130 include all known electroluminescent materials. Organometallic electroluminescent compounds are preferred. The most preferred compounds include cyclometalated iridium and platinum electroluminescent compounds and mixtures thereof. Complexes of Iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescentdeviceswith an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. Examples of a few suitable iridium complexes are given in FIG. 6, as Formulae IV(a) through IV(e). Analogous tetradentate platinum complexes can also be used. These electroluminescent complexes can be used alone, or doped into charge-carrying hosts, as noted above. The molecules of the present invention, in addition to being useful in the hole transport layer 120, may also act as a charge carrying host for the emissive dopant in the photoactive layer 130.

Examples of electron transport materials which can be used in layer 140 and/or layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency with device operational lifetime.

It is understood that each functional layer may be made up of more than one layer.

The device can be prepared by a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied from solutions or dispersions in suitable solvents, using any conventional coating or printing technique, including but not limited to spin-coating, dip-coating, roll-to-roll techniques, ink-jet printing, screen-printing, gravure printing and the like. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layer 140 and 150, 50-2000 Å, preferably 100-1000 Å; cathode 160, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

The triarylmethane derivative compounds of the invention may be useful in applications other than OLEDs. For example, these compositions may be used in photovoltaic devices for solar energy conversion. They may also be used in field effect transistor for smart card and thin film transistor (TFT) display driver applications.

EXAMPLES

The following examples illustrate certain features and advantages of the present invention. They are intended to be illustrative of the invention, but not limiting. All percentages are by weight, unless otherwise indicated.

Example 1

This example illustrates the preparation of triarylmethane hole transport compositions, shown in FIG. 3.

Compound I(f): 32.6 g of N,N-diethyl-m-toluidine and 12.4 g p-fluorobenzaldehyde were mixed in 30 mL ethanol and 10 mL conc. HCl. This mixture was gently refluxed under nitrogen for 16 hrs at which point the mixture was cooled and poured into 250 mL distilled water. The solution was adjusted to pH 8 with sodium hydroxide (1 M) solution and the ethanol removed by rotovap. The aqueous layer was decanted from the solid residue which was then washed with 100 mL distilled water and finally recrystallized from hot ethanol. The crystalline white solid was dried in vacuo and then tested for OLED device utility. Yield 46%; 1H nmr (CDCl3): 6.9(m); 6.82(t); 6.45(m); 6.35(m); 5.38(s); 3.23(q); 2.02(s); 1.05(t). 19F nmr: −118.6(s); MPt 100 C Other triarylmethane compounds were made similarly substituting on equivalent of the appropriate aldehyde for p-fluorobenzaldehyde in the above procedure.

Compound I(a): Yield 58%; MPt 113 C; 1H nmr: 7.1(t); 7.0(t); 6.9(d); 6.4(d); 6.35(s); 6.28(d); 5.37(s); 3.15(q); 1.97(s); 1.0(t)

Compound I(b): Yield 64%; MPt 167° C.; 1H nmr: 7.45(d); 7.1 (d); 6.4(m); 6.35(m); 5.45(s); 3.23(q); 2.02(s); 1.05(t)

Compound I(c): Yield 79%; MPt 161° C.; 1H nmr: 8.10(d); 7.16(d); 6.4(m); 6.35(m); 5.50(s); 3.23(q); 2.02(s); 1.05(t)

Compound I(d): Yield 62%; MPt 143° C.; 1H nmr: 7.38(d); 6.97(d); 6.54(m); 6.42(m); 5.47(s); 3.35(q); 2.12(s); 1.15 (t)

Compound I(e): Yield 48%; MPt 96° C.; 1H nmr: 6.88(d); 6.71 (d); 6.5(d); 6.41 (m); 6.3(m); 5.35(s); 3.23(q); 2.02(s); 1.05(t)

Compound I(g): Yield 3%; MPt. 155° C.; 1H nmr: 6.95(d); 6.72(d); 6.62(d); 6.55(m); 6.45(m); 5.45(s); 4.64(s); 3.33 (q); 2.12(s); 1.15(t)

Compound I(h): Yield 14%; MPt. 139° C.; 1H nmr: 6.80(d); 6.6(d); 6.5(m); 6.38(m); 5.33(s); 2.80(s); 2.06(s)

Compound I(i): Yield 40%; MPt. 163° C.; 1H nmr: 7.16(d); 6.87(d); 6.51 (d); 6.40(s); 6.32(d); 5.38(s); 3.23(q); 2.02(s); 1.21(s); 1.05(t)

Compound I(j): Yield 59%; MPt. 159° C.; 1H nmr: 7.51(d); 7.38(d); 7.33(t); 7.22(t) 7.05(d) 6.54(d); 6.43(s); 6.35(d); 5.45(s); 3.23(q); 2.02(s); 1.05(t)

Compound I(k): Yield 7%; MPt. 198° C.; 1H nmr: 6.70(d); 6.42(m); 5.68(s); 3.23(q); 2.02(s); 1.05(t); 19F nmr: −140.6(m); −158.0(m); −163.0(m)

Compound I(l): Yield 98%; MPt. 122 C; 1H nmr: 7.18(d); 7.13(s); 7.00(t); 6.85(d); 6.42(d); 6.39(s); 6.30(m); 5.35(s); 3.23(q); 2.02(s); 1.05(t)

Compound I(m): Yield 68%; MPt. 147 C; 1H nmr: 7.30(d); 6.96(d); 6.32(m); 6.24(m); 5.34(s); 3.13(q); 1.95(s); 1.00 (t); 19F nmr: −62.6(s)

Compound I(n): Yield 57%; MPt. 150 C; 1H nmr: 7.20(m); 6.88(m); 6.4(m); 6.35(m); 5.38(s); 3.23(q); 2.02(s); 1.05 (t); 19F nmr: −112.6(s)

Compound I(o): Yield 41%; MPt. 135 C; 1H nmr: 8.58(d); 7.79(d); 7.6(m); 7.1(d); 6.54(d); 6.42(s); 6.35(d); 5.47(s); 3.23(q); 2.02(s); 1.05(t)

Compound I(p): Yield 43%; MPt. 111 C; 1H nmr: 7.50(s); 6.4(m); 6.35(m); 5.50(s); 3.23(q); 2.02(s); 1.05(t); 19F nmr: −108.1 (s); −108.5(s).

Example 2

This examples illustrates the preparation of a hole transport compound having multiple triarylmethane groups, Compound II(c) in FIG. 5.

Step 1:

1,3,5,7-Tetraphenyl adamantane was prepared according to Newman, H., *Synthesis* 1972, 692.

In a dry box: to a 100-mL, jacketed, one-neck, round-bottom flask equipped with a magnetic stirring bar and NaOH drying tube, was added 1,3,5,7-tetraphenyladamantane (1.00 g, 2.27 mmol) and 30 mL anhydrous methylene chloride. The undissolved reaction mixture was cooled to −5° C. and then charged with $TiCl_4$ (3.38 mL, 30.82 mmol) and then dichloromethylmethylether (3.38 mL, 37.37 mL). The reaction stirred 17 h. at −5° C. and was then poured into crushed ice. The aqueous layer was diluted to 300 mL, vigorously shaken and the layers then separated. The organic layer was then washed with 200-mL brine, dried over $MgSO_4$ and then concentrated to afford a yellow solid. The crude material was dissolved in hot ethyl acetate, and then diluted with hexane until the formation of a precipitate was observed. The mixture was filtered, the precipitate discarded, and the filtrate concentrated by rotary evaporation, affording 0.5520 g of a white waxy solid.

Step 2:

A 100-mL, one-neck, round-bottom flask, equipped with magnetic stirring bar, Dean-Stark trap, condenser, and nitrogen inlet was charged with 1,3,5,7-adamantane tetrakisbenzaldehyde (0.55 g, 1.0 mmol), 60 mL n-butanol, 20 mL conc. HCl, and N,N-diethyl-m-toluamide (0.666 g, 4.08 mmol). The reaction mixture was heated at reflux for 24 h. and then water was azeotropically distilled over an additional 16 h. The remaining green solution was concentrated by rotary evaporation, dissolved in 150 mL methylene chloride and washed with 150 mL water. The aqueous layer was adjusted to pH 8 by addition of a saturated solution of sodium bicarbonate. The mixture was shaken, the layers separated, the organic layer dried over $MgSO_4$, and then concentrated by rotary evaporation affording 1.4958 g of a brown glassy solid. Purification by flash chromatography over silica gel (2.5% i-PrOH in $CH_2Cl_2$) afforded 0.8977 g of a tan glassy solid.

Example 3

This example illustrates the preparation of an iridium electroluminescent complex, shown as Formula IV(a) in FIG. 6.

Phenylpyridine ligand,
2-(4-fluorophenyl)-5-trifluoromethylpyridine

The general procedure used was described in O. Lohse, P. Thevenin, E. Waldvogel *Synlett,* 1999, 45-48. A mixture of 200 ml of degassed water, 20 g of potassium carbonate, 150 ml of 1,2-dimethoxyethane, 0.5 g of $Pd(PPh_3)_4$, 0.05 mol of 2-chloro -5-trifluoromethylpyridine and 0.05 mol of 4-fluorophenylboronic acid was refluxed (80-90° C.) for 16-30 h. The resulting reaction mixture was diluted with 300 ml of water and extracted with $CH_2Cl_2$ (2×100 ml). The combined organic layers were dried over $MgSO_4$, and the solvent removed by vacuum. The liquid products were purified by fractional vacuum distillation. The solid materials were recrystallized from hexane. The typical purity of isolated materials was >98%.

Iridium Complex:

A mixture of $IrCl_3.nH_2O$ (54% Ir; 508 mg), 2-(4-fluorophenyl)-5-trifluoromethylpyridine, from above (2.20 g), $AgOCOCF_3$ (1.01 g), and water (1 mL) was vigorously stirred under a flow of $N_2$ as the temperature was slowly (30 min) brought up to 185° C. (oil bath). After 2 hours at 185-190° C. the mixture solidified. The mixture was cooled down to room temperature. The solids were extracted with dichloromethane until the extracts decolorized. The combined dichloromethane solutions were filtered through a short silica column and evaporated. After methanol (50 mL) was added to the residue the flask was kept at −10° C. overnight. The yellow precipitate of the tris-cyclometalated complex, compound IVa, was separated, washed with methanol, and dried under vacuum. Yield: 1.07 g (82%). X-Ray quality crystals of the complex were obtained by slowly cooling its warm solution in 1,2-dichloroethane.

Example 4

This example illustrates the formation of OLEDs using the charge transport compositions of the invention.

Thin film OLED devices including a hole transport layer (HT layer), electroluminescent layer (EL layer) and at least one electron transport and/or anti-quenching layer (ET/AQ layer) were fabricated by the thermal evaporation technique. An Edward Auto 306 evaporator with oil diffusion pump was used. The base vacuum for all of the thin film deposition was in the range of $10^{-6}$ torr. The deposition chamber was capable of depositing five different films without the need to break up the vacuum.

Patterned indium tin oxide (ITO) coated glass substrates from Thin Film Devices, Inc was used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to $10^{-6}$ torr. The substrate was then further cleaned using an oxygen plasma for about 5-10 minutes. After cleaning, multiple layers of thin films were then deposited sequentially onto the substrate by thermal evaporation. Finally, patterned metal electrodes of Al or LiF and Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

Table 1 summarizes the devices made with the hole transport compositions of the invention, and with the comparative hole transport compounds shown in FIG. 8. In all cases emitting layer was the iridium complex from Example 3, having the thickness indicated. The electron transport layer 140 was 4,7-diphenyl-1,10-phenanthroline, DPA. When present, electron transport layer 150 was tris(8-hydroxyquinolato)aluminum(III), Alq, each having the thicknesses given. The cathode was a layer of Al or a dual layer of LiF/Al, with the thickness given.

TABLE 1

| Devices | | | | | |
|---|---|---|---|---|---|
| Sample | HT (A) | EL, Å | ET/AQ, Å | ET, Å | Cathode, Å |
| Comparative A | Comp. A 509 | 405 | DPA 103 | Alq 305 | LiF 10 Al 512 |
| Comparative B | Comp. B 510 | 403 | DPA 411 | | Al 735 |
| Comparative C | Comp. C 506 | 433 | DPA 414 | | Al 734 |
| Comparative D | Comp. D 505 | 412 | DPA 417 | | Al 726 |
| Comparative E | Comp. E 302 | 404 | DPA 101 | Alq 304 | LiF 10 Al 453 |
| 1-1 | I(a) 302 | 402 | DPA 101 | Alq 302 | LiF 10 Al 453 |
| 1-2 | I(b) 303 | 403 | DPA 103 | Alq 304 | LiF 10 Al 452 |
| 1-3 | I(c) 303 | 403 | DPA 101 | Alq 303 | LiF 10 Al 454 |
| 1-4 | I(d) 303 | 405 | DPA 101 | Alq 303 | LiF 10 Al 454 |
| 1-5 | I(e) 303 | 404 | DPA 101 | Alq 303 | LiF 10 Al 453 |
| 1-6 | I(f) 303 | 404 | DPA 102 | Alq 302 | LiF 10 Al 452 |
| 1-7 | I(g) 304 | 405 | DPA 103 | Alq 302 | LiF 10 Al 452 |
| 1-8 | I(h) 302 | 403 | DPA 102 | Alq 302 | LiF 10 Al 453 |
| 1-9 | I(i) 305 | 404 | DPA 105 | Alq 302 | LiF 10 Al 453 |
| 1-10 | I(j) 305 | 403 | DPA 102 | Alq 303 | LiF 10 Al 453 |
| 1-11 | I(k) 304 | 403 | DPA 101 | Alq 303 | LiF 10 Al 317 |
| 1-12 | I(l) 301 | 403 | DPA 100 | Alq 302 | LiF 10 Al 330 |

TABLE 1-continued

| Devices | | | | | |
|---|---|---|---|---|---|
| Sample | HT (A) | EL, Å | ET/AQ, Å | ET, Å | Cathode, Å |
| 1-13 | I(m) 302 | 405 | DPA 102 | Alq 305 | LiF 10 Al 453 |
| 1-14 | I(n) 302 | 403 | DPA 102 | Alq 303 | LiF 10 Al 451 |
| 1-15 | II(a) 302 | 404 | DPA 102 | Alq 304 | LiF 10 Al 452 |
| 1-16 | II(b) 302 | 402 | DPA 101 | Alq 301 | LiF 10 Al 454 |

Figure 9:
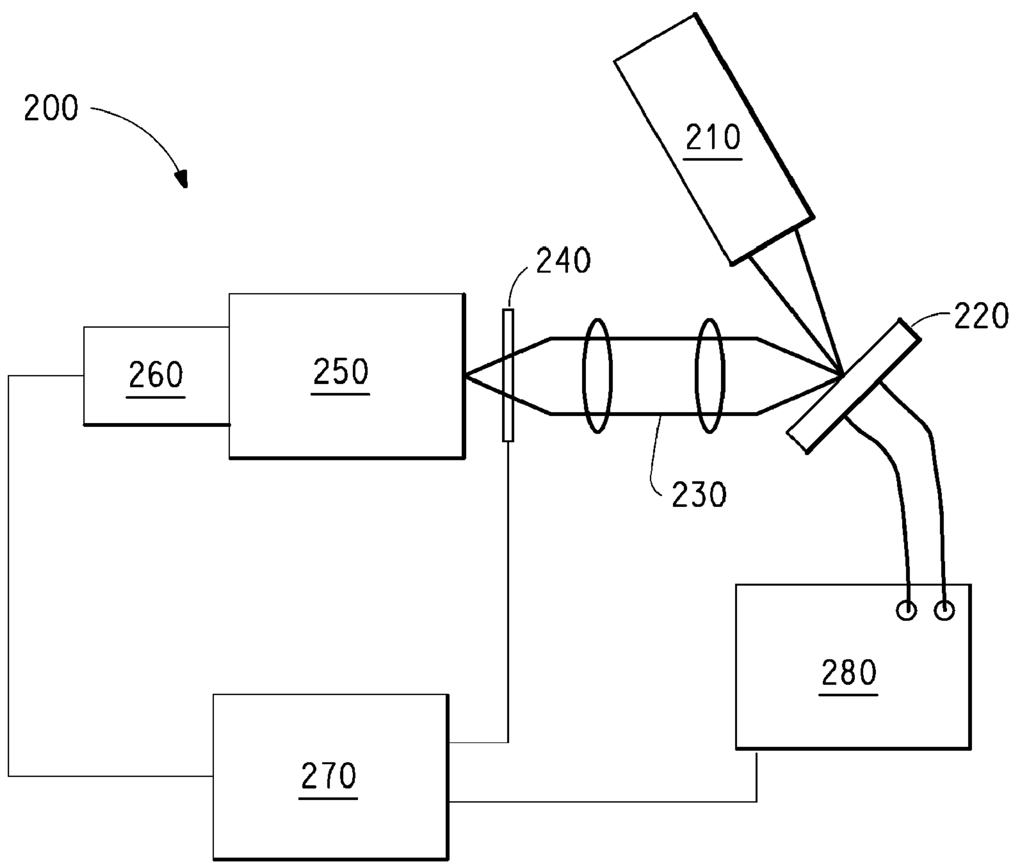
FIG. 9 is a schematic diagram of a testing device for an LED.

The OLED samples were characterized by measuring their (1) current-voltage (I-V) curves, (2) electroluminescence radiance versus voltage, and (3) electroluminescence spectra versus voltage. The apparatus used, 200, is shown in FIG. 9. The I-V curves of an OLED sample, 220, were measured with a Keithley Source-Measurement Unit Model 237, 280. The electroluminescence radiance (in the unit of cd/m$^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in cd/A.

The results for devices using the triarylmethane hole transport compositions of the invention are given in Table 2 below:

TABLE 2

| Electroluminescent Properties of Devices | | |
|---|---|---|
| Sample | Peak Radiance, cd/m2 | Peak efficiency, cd/A |
| Comp. A | 7000 at 14 V | 24 |
| Comp. B | 3700 at 21 V | 16 |
| Comp. C | 500 at 17 V | 1.1 |
| Comp. D | 1500 at 16 V | 1.5 |
| Comp. E | 18000 at 11 V | 12 at 9 V; 8 lm/W at 5 V |
| 1-1 | 6000 at 15 V | 22 |
| 1-2 | 6000-7400 at 17 V | 14-17 |
| 1-3 | 40 at 23 V | .25 |
| 1-4 | 700 at 13 V | 6-10 |
| 1-5 | 7000 at 15 V | 20 |
| 1-6 | 11000 at 13 V | 35 |
| 1-7 | 3700 at 15 V | 10 |
| 1-8 | 2600 at 15 V | 11.5 |
| 1-9 | 4000 at 16 V | 20 at 11 V |
| 1-10 | 3400 at 16 V | 5 at 12 V |
| 1-11 | 800 at 14 V | 10 at 13 V |
| 1-12 | 110 at 12 V | 20 at 10 V |
| 1-13 | 450 at 10 V | 8 at 10 V |
| 1-14 | 250 at 9 V | 9 at 10 V |

TABLE 2-continued

Electroluminescent Properties of Devices

| Sample | Peak Radiance, cd/m2 | Peak efficiency, cd/A |
|---|---|---|
| 1-15 | 1500-2000 at 18 V | 6.5 at 14 V |
| 1-16 | 1000-1500 at 18 V | 5.5 at 12 V |

Example 5

This example illustrates the preparation of Compound I(q) in FIG. 3.

1.2 g tolualdehyde and 5.8 g m-dibenzylamino-toluene were mixed in 3 mL ethanol and 1 mL concentrated HCl. The mixture was then gently refluxed under nitrogen for 2 days. The resulting material was poured into 25 mL water and the pH was adjusted to 8 with sodium hydroxide solution (1 N). The ethanol solvent was rotovaporated and the aqueous supernatant was decanted from the greenish organic layer. The organic layer was triturated with dry ethanol until it became a greenish solid. After recrystallization from boiling ethanol, the material was rapidly chromatographed on neutral alumina using methylene chloride eluent to remove colored impurities and aldehyde contaminants. The resulting white solid was collected and dried in vacuum. Yield 1.0 g ~15%.

Example 6

This example illustrates the preparation of Compound II(d) in FIG. 5.

12.5 g iso-phthalaldehyde and 59.0 g m-diethylamino-toluene were mixed in 55 mL ethanol and 18 mL concentrated HCl. The mixture was then gently refluxed under nitrogen for 60 hrs. The resulting material was poured into 100 mL water and the pH was adjusted to 8 with sodium hydroxide solution (1 N). The ethanol solvent was rotovaporated and the aqueous supernatant was decanted from the greenish organic layer. The organic layer washed with 100 mL distilled water and then triturated with dry ethanol until it became a greenish solid. After recrystallization from boiling ethanol, the material was rapidly chromatographed on neutral alumina using methylene chloride eluent to remove colored impurities and aldehyde contaminants. The resulting white solid was collected and dried in vacuum. Yield 25.5 g ~39%.

Example 7

This example illustrates the preparation of Compound I(r) in FIG. 3.

14.0 g diphenylamino-p-benzaldehyde and 16.3 g m-diethylamino-toluene were mixed in 15 mL ethanol and 5 mL concentrated HCl. The mixture was then gently refluxed under nitrogen for 48 hrs. The resulting material was poured into 25 mL water and the pH was adjusted to 8 with sodium hydroxide solution (1 N). The ethanol solvent was rotovaporated and the aqueous supernatant was decanted from the bluish organic layer. The organic layer washed with 100 mL distilled water and then triturated with dry ethanol until it became a tan colored solid. After recrystallization from boiling ethanol, the material was rapidly chromatographed on neutral alumina using methylene chloride eluent to remove colored impurities and aldehyde contaminants. The resulting white solid was collected and dried in vacuum. Yield 9.0 g ~31%.

Example 8

This example illustrates the preparation of Compound I(s) in FIG. 3.

5.0 g 3-vinylbenzaldehyde and 11.0 g m-diethylamino-toluene were mixed in 10 mL ethanol and 3.4 mL concentrated HCl. The mixture was then gently refluxed under nitrogen for 48 hrs. The resulting material was poured into 25 mL water and the pH was adjusted to 8 with sodium hydroxide solution (1 N). The ethanol solvent was rotovaporated and the aqueous supernatant was decanted from the greenish organic layer. The organic layer washed with 100 mL distilled water and then triturated with dry ethanol until it became a tan colored solid. After recrystallization from boiling ethanol, the material was rapidly chromatographed on neutral alumina using methylene chloride eluent to remove colored impurities and aldehyde contaminants. The resulting white solid was collected and dried in vacuum. Yield 4.5 g ~34%.

Example 9

This example illustrates the preparation of Compound II(e) in FIG. 5.

2.64 g 3,5-dibromobenzaldehyde, 3.0 g 4-formylboronic acid, 0.4 g tetrakistriphenylphosphine palladium, 3.2 g potassium carbonate, 40 mL water and 40 mL dimethoxyethane was combined under nitrogen and refluxed for 20 hrs. After cooling to room temperature the organic layer was collected and the aqueous layer was extracted 3× with 25 mL portions of methylene chloride. All extracts and organic layer were combined and dried over magnesium sulfate before filtering and evaporating to dryness. The resultant product trialdehyde was isolated and characterized by nmr in yield of 2.6 g ~84%.

The trialdehyde material 2.6 g was combined with 8.1 g m-diethylamino-toluene and mixed in 7.5 mL ethanol and 2.5 mL concentrated HCl. The mixture was then gently refluxed under nitrogen for 48 hrs. The resulting material was poured into 25 mL water and the pH was adjusted to 8 with sodium hydroxide solution (1 N). The ethanol solvent was rotovaporated and the aqueous supernatant was decanted from the olive green organic layer. The organic layer washed with 100 mL distilled water and then triturated with dry ethanol until it became a tan colored solid. After recrystallization from boiling ethanol, the material was rapidly chromatographed on neutral alumina using methylene chloride eluent to remove colored impurities and aldehyde contaminants. The resulting white solid was collected and dried in vacuum. Yield 1.2 g ~15%.

Example 10

This example illustrates the preparation of Compound II(f) in FIG. 5.

3.15 g 1,3,5-tribromobenzene, 4.5 g 4-formylboronic acid, 0.6 g tetrakistriphenylphosphine palladium, 4.8 g potassium carbonate, 60 mL water and 60 mL dimethoxyethane was combined under nitrogen and refluxed for 20 hrs. After cooling to room temperature the organic layer was collected and the aqueous layer was extracted 3× with 25 mL portions of methylene chloride. All extracts and organic layer were combined and dried over magnesium sulfate before filtering and evaporating to dryness. The resultant product trialdehyde was isolated and characterized by nmr in yield of 3.8 g ~95%.

The trialdehyde material 3.8 g was combined with 9.8 g m-diethylamino-toluene and mixed in 9 mL ethanol and 3 mL concentrated HCl. The mixture was then gently refluxed under nitrogen for 48 hrs. The resulting material was poured into 25 mL water and the pH was adjusted to 8 with sodium hydroxide solution (1 N). The ethanol solvent was rotovaporated and the aqueous supernatant was decanted from the olive green organic layer. The organic layer washed with 100 mL distilled water and then triturated with dry ethanol until it became a tan colored solid. After recrystallization from boiling ethanol, the material was rapidly chromatographed on neutral alumina using methylene chloride eluent to remove colored impurities and aldehyde contaminants. The resulting white solid was collected and dried in vacuum. Yield 1.3 g ~10%.

Example 11

This example illustrates the preparation of Compound I(t) in FIG. 3, using the reaction scheme shown below.

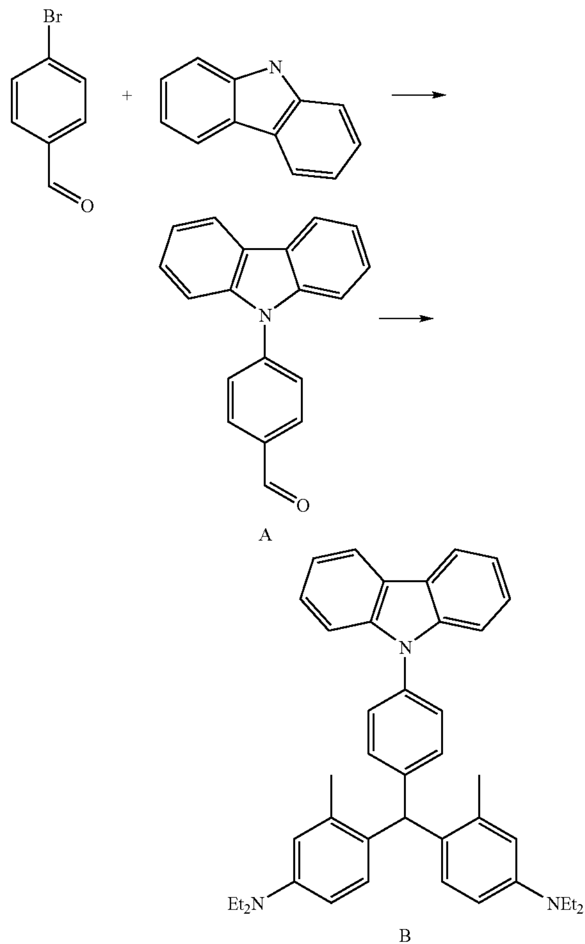

Precursor Compound A:

Under an atmosphere of nitrogen, a 40 mL vial was charged with 4-bromobenzaldehyde (3.478 g, 0.0188 mol), carbazole (3.013 g, 0.0179 mol), $Pd(OAc)_2$ (0.0402 g, $1.79\times10^{-4}$ mol), $P(t\text{-}Bu)_3$ (0.1086 g, $5.37\times10^{-4}$ mol), $K_2CO_3$ (7.422 g, 0.0537 mol) and 20 mL o-xylene. The reaction mixture was heated (100 C) for two days. The resulting mixture was filtered through a plug of silica using hexane, followed by 25% EtOAc/hexane and finally hexane. Volatiles were evaporated to give a pale-yellow solid, which washed with hot MeOH (20 mL) and hexane (20 mL). The desired product was isolated as a white powder in 29% yield (1.406 g).

Compound I(t):

Under an atmosphere of nitrogen, a 50 mL three-neck flask was charged with precursor compound A (1.000 g, 5.98 mmol), N,N-diethyl-m-toluidine (2.12 mL, 11.9 mmol), conc. HCl (1 mL) and EtOH (2 mL). The resulting mixture was refluxed for three days. After cooling to room temperature, the solution was diluted with 25 mL $H_2O$ and adjusted the pH to 9 using 50% NaOH solution. The volatiles were removed by rotary evaporation and the product was purified by chromatography (7% EtOAc/hexane) to give 0.91 g (26% yield).

Example 12

This example illustrates the preparation of Compound II(g) in FIG. 5, using the reaction scheme shown below.

Under an atmosphere of nitrogen, a round bottom flask was charged with a THF (48 mL) solution of tris(4-bromophenyl) amine (4.82 g, mmol) and cooled to −70 C, to which nBuLi (1.6 M in hexane, 20 mL, 32 mmol) was slowly added. After 45 minutes, N,N-dimethylformamide (5.0 mL) was added and the reaction solution was allowed to slowly warm up to 5 C. After quenching with HCl (12.5 mL conc. HCl in 50 mL $H_2O$), the resulting mixture was allowed to stir at room temperature overnight. The aldehyde precursor A was isolated by extraction with $CH_2Cl_2$ as a yellow solid, which can be purified by washing with hexane to give the pure product in 90% yield (2.97 g). $^{13}C$ NMR ($CD_2Cl_2$): δ 125.33, 131.83, 133.45, 152.0, 191.17

A mixture of 3.43 g (21 mmol) of N,N-diethyl-m-toluidine, 0.988 g (3 mmol) above aldehyde precursor A in 5 mL n-propanol and 0.25 mL methane sulfonic acid were added to round-bottom flask equipped with a Dean-Stark trap. This mixture was gently refluxed under nitrogen for 72 h. The product, compound II(g), was isolated as described in Example 1 to give a 1.80 g (48%) of a off-white powder. $^1$H NMR ($CD_2Cl_2$): δ 6.85(m);

6.55(d), 6.45(m), 6.30(m), 5.30(s), 3.70(s), 3.20(q), 2.00(s), 1.0 (t).

Example 13

This example illustrates the preparation of Compound II(h) in FIG. 5, using the reaction scheme shown below.

A mixture of 1.63 g (0.01 mol) of N,N-diethyl-m-toluidine, 1.052 g (0.0022 mol) above aldehyde precursor C in 12 mL n-propanol and 0.05 g methane sulfonic acid were added to round-bottom flask equipped with a Dean-Stark trap. This mixture was gently refluxed under nitrogen for 48 h. The product, compound II(h), was isolated as described in Example 1 and was purified by extraction from hot hexane to give a 1.03 g (42%) of a yellow powder. $^1$H NMR ($CD_2Cl_2$): δ 7.230 (t), 7.074-6.925(m), 6.609(broad d), 6.502(s), 6.413 (broad d), 5.428(s), 3.306(d), 2.140(s), 1.126 (t). Anal. Calcd. for $C_{76}H_{88}N_6$: C, 84.09; H, 8.17; N, 7.74. Found: C, 84.19, H, 8.37; N, 7.69.

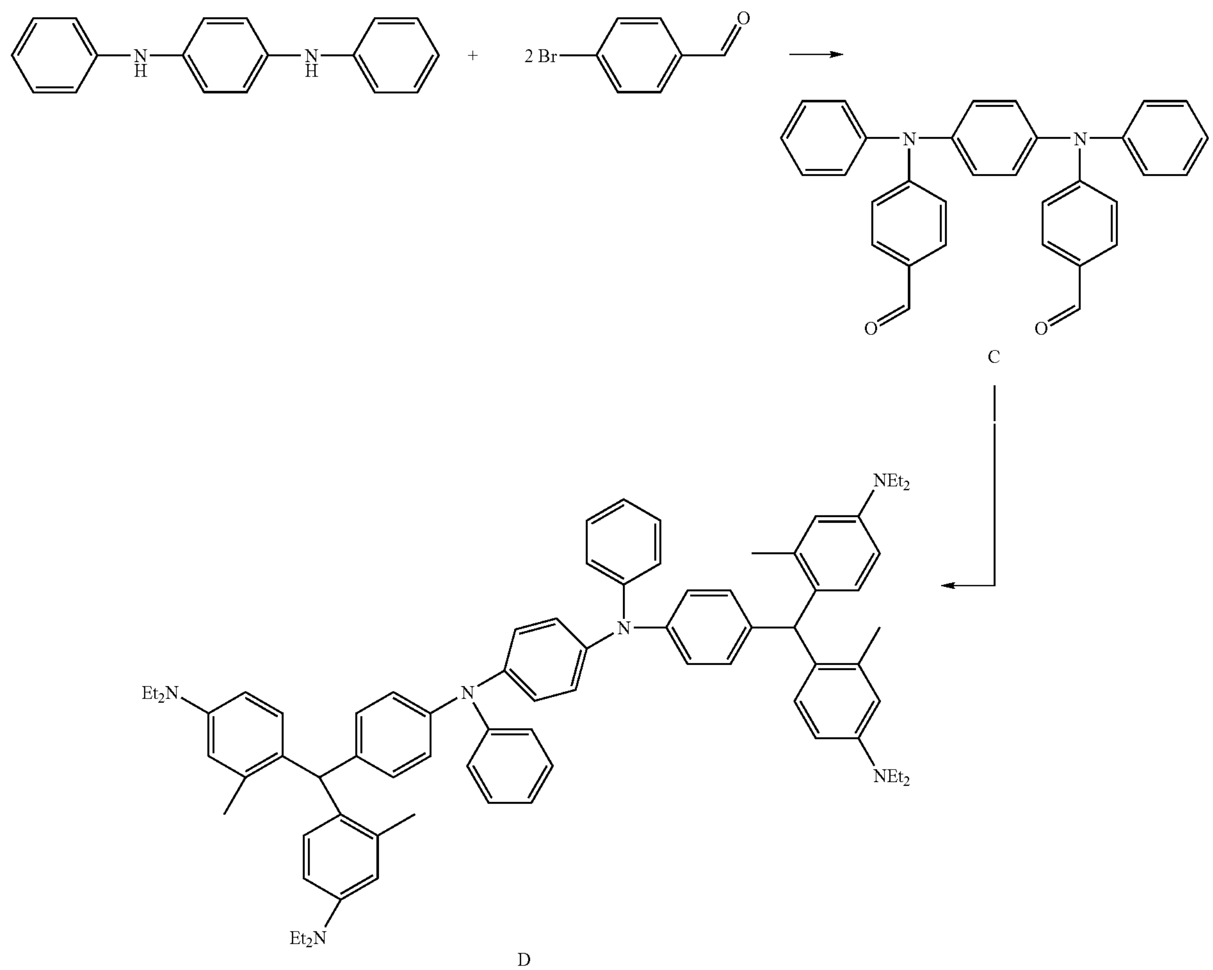

Under an atmosphere of nitrogen, a round bottom flask equipped with a condenser was charged with $Pd_2(dba)_3$ (0.88 g, 0.96 mmol), BINAP (0.62 g, 0.99 mmol), $Cs_2CO_3$ (9.38 g, 0.029 mol), 4-bromobenzaldehyde (8.17 g, 0.04 mol), N,N'-Diphenyl-1,4-phenylenediamine (5.02 g, 0.019 mol) and toluene (100 mL). The mixture was heated to 100 C for four days. The reaction was cooled to room temperature, diluted with EtOAc (200 mL) and filtered through a pad of silica. Upon evaporation of volatiles the crude material was obtained as a dark brown oil, which was purified by silica gel chromatography (1/3 EtOAc/hexane) to give aldeyhyde precursor C as a yellow powder in 51% yield (4.64 g). Anal. Calcd. for $C_{32}H_{24}N_2O_2$: C, 82.03; H, 5.16; N, 5.98. Found: C, 79.7; H, 5.40; N, 5.55.

What is claimed is:

1. An electronic device comprising at least one layer comprising a triarylmethane derivative having Formula I, wherein:

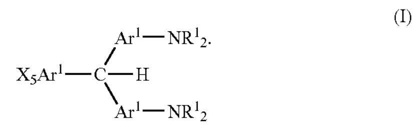

(I)

$Ar^1$ can be the same or different at each occurrence and is selected from the group consisting of aryl and heteroaryl;

$R^1$ is the same or different at each occurrence and is selected from the group consisting of H, alkyl, heteroalkyl, aryl, heteroaryl, arylalkylene, heteroarylalkylene, arylalkylene, heteroarylalkylene, $C_nH_aF_b$, and $C_6H_cF_d$, or adjacent $R^1$ groups can be joined to form 5- or 6-membered rings;

X can be the same or different at each occurrence and is selected from the group consisting of H, alkenyl, alkynyl, $N(R^1)_2$, $OC_6H_cF_d$, CN, $COOR^1$, NO2 a fused heterocyclic ring, and OH, where at least one X is not H;

n is an integer from 1 through 12, and a, b, c, and d are 0 or an integer, such that a+b=2n+1, and c+d=5, with the proviso that when $X_5Ar^1$ is p-methylphenylene, $R^1$ is not ethyl, wherein the device is selected from the group consisting of a light-emitting diode, a light-emitting electrochemical cell, and a photodetector.

2. The device of claim 1, wherein $Ar^1$ is selected from the group consisting of phenyl, substituted phenyl, biphenyl, and substituted biphenyl.

3. The device of claim 2 wherein $Ar^1$ is selected from the group consisting of substituted phenyl and substituted biphenyl having at least one substituent selected from alkyl, heteroalkyl, aryl, heteroaryl, arylalkylene, heteroarylalkylene, $C_nH_aF_b$, and $C_6H_cF_d$, where a, b, c, and d are 0 or an integer, such that a+b=2n+1, and c+d=5, and n is an integer.

4. The device of claim 1 wherein $Ar^1$ is selected from the group consisting of phenyl, substituted phenyl, biphenyl, and substituted biphenyl, wherein at least one carbon atom is replaced with a heteroatom.

5. The device of claim 1 wherein $Ar^1$ of $X_5Ar^1$ is selected from the group consisting of phenyl, substituted phenyl, biphenyl, substituted biphenyl, pyridyl, substituted pyridy, bipyridyl, and substituted bipyridyl.

6. The device of claim 5 wherein $Ar^1$ is selected from the group consisting of substituted phenyl, substituted biphenyl, and substituted pyridyl, having at least one substituent selected from, heteroalkyl, aryl, heteroaryl, arylalkylene, heteroarylalkylene, $C_nH_aF_b$, and $C_6H_cF_d$, where a, b, c, and d are 0 or an integer, such that a+b=2n+1, and c+d=5, and n is an integer.

7. The device of claim 1, wherein at least one substituent on an aryl ring is selected from the group consisting of F, $C_nH_aF_b$, $OC_nH_aF_b$, $C_6H_cF_d$, and $OC_6H_cF_d$, where a, b, c, and d are 0 or an integer, such that a+b=2n+1, and c+d=5, and n is an integer.

8. The device of claim 1, wherein at least one X group is selected from the group consisting of F, $C_nH_aF_b$, $OC_nH_aF_b$, $C_6H_cF_d$, and $OC_6H_cF_d$, where a, b, C, and d are 0 or an integer, such that a+b=2n+1, and c+d=5, and n is an integer.

9. An electronic device having at least one of a hole transport layer and a photoactive layer which comprises a triarylmethane derivative, wherein the triarylmethane derivative is selected from triarylmethane derivatives recited in claim 1.

10. A device of claim 9, wherein the device is selected from the group consisting of a light-emitting diode, a light-emitting electrochemical cell, and a photodetector.

11. The device of claim 1 wherein X is a fused heterocyclic ring group.

12. The device of claim 11 wherein X is selected from the group consisting of N-carbazoles, benzodiazoles, and benzotriazoles.

13. An electronic device comprising at least one layer comprising a charge transport composition comprising a triarylmethane having Formula I, wherein:

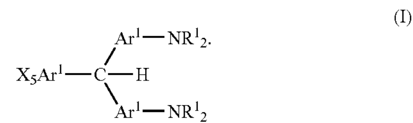

(I)

$Ar^1$ can be the same or different at each occurrence and is selected from the group consisting of aryl and heteroaryl;

$R^1$ is the same or different at each occurrence and is selected from the group consisting of H, alkyl, heteroalkyl, aryl, heteroaryl, $C_nH_aF_b$, and $C_6H_CF_d$, X can be the same or different at each occurrence and is selected from the group consisting of $R^1$, alkenyl, alkynyl, $N(R^1)_2$, $OR^1$, $OC_nH_aF_b$, $OC_6H_cF_d$, CN, $COOR^1$, halide, NO2, and OH;

n is an integer from 1 through 12, and a, b, c, and d are integers such that a+b =2n+1, and c+d=5, wherein b and d are not 0 with the proviso that there is at least one substituent on an aromatic group selected from F, $C_nH_aF_b$, $OC_nH_aF_b$, $C_6H_cF_d$, and $OC_6H_cF_d$.

* * * * *